(12) United States Patent
Allen et al.

(10) Patent No.: US 6,316,024 B1
(45) Date of Patent: Nov. 13, 2001

(54) THERAPEUTIC LIPOSOME COMPOSITION AND METHOD OF PREPARATION

(75) Inventors: Theresa M. Allen, Edmonton (CA); Paul Uster, Tracy, CA (US); Francis J. Martin, San Francisco, CA (US); Samuel Zalipsky, Redwood City, CA (US)

(73) Assignee: Sequus Pharmaceuticals, Inc.

( * ) Notice: Subject to any disclaimer, the term of this patent is extended or adjusted under 35 U.S.C. 154(b) by 0 days.

(21) Appl. No.: 09/517,224

(22) Filed: Mar. 2, 2000

Related U.S. Application Data

(60) Division of application No. 09/138,480, filed on Aug. 21, 1998, now Pat. No. 6,056,973, which is a continuation-in-part of application No. 08/949,046, filed on Oct. 10, 1997, now Pat. No. 5,891,468.
(60) Provisional application No. 60/028,269, filed on Oct. 11, 1996.

(51) Int. Cl.[7] .................................................. A61K 9/127
(52) U.S. Cl. ........................ 424/450; 436/829; 424/812; 935/54
(58) Field of Search ..................... 424/450, 812, 424/1.21, 9.321, 9.51, 417, 94.3; 430/829; 935/54

(56) References Cited

U.S. PATENT DOCUMENTS

| | | |
|---|---|---|
| 5,013,556 | 5/1991 | Woodle et al. . |
| 5,370,993 | 12/1994 | Tarnowski et al. . |
| 5,395,619 | 3/1995 | Zalipsky . |
| 5,620,689 | 4/1997 | Allen et al. . |
| 5,631,018 | 5/1997 | Zalipsky . |

FOREIGN PATENT DOCUMENTS

| | | |
|---|---|---|
| 354 855 A2 | 2/1990 | (EP) . |
| 526 700 A2 | 2/1993 | (EP) . |
| 7173079 | 7/1995 | (JP) . |
| WO 91/05545 | 5/1991 | (WO) . |

OTHER PUBLICATIONS

Blumberg, B.M., et al., "Sequence Determination of the Sendai Virus Fusion Protein Gene" *J. Gen. Virol.* 66:317–331 (1985).

Collins, P.L., et al., "Nucleotide Sequence of the Gene Encoding the Fusion (F) Glycoprotein of Human Respiratory Syncytial Virus" *Proc. Natl. Acad. Sci. USA* 81:7683–7687 (1984).

Durell, S.R., et al., "What Studies of Fusion Peptides tell us about Viral Envelope Glycoprotein mediated Membrane Fusion (review)" *Molecular Membrane Biology* 14:97–112 (1997).

Düzgünes, N., et al., "Fusion of Liposomes Containing a Novel Cationic Lipid, N–[2,3–(Dioleyloxy)propyl]–N,N,N–trimethylammonium: Induction by Multivalent Anions and Asymmetric Fusion with Acidic Phospholipid Vesicles" *Biochemistry.* 28: 9179–9184 (1989).

Hsu, M–c., and Choppin, P.W., "Analysis of Sendai Virus mRNAs with cDNA Clones of Viral Genes and Sequences of Biologically Important Regions of the Fusions Protein" *Proc. Natl. Acad. Sci. USA* 81: 7732–7736 (1984).

Kielian, M., "Membrane Fusion Activity of Alphaviruses" *Viral Fusion Mechanisms* J. Bentz (ed), CRC Press: Boca Raton, pp. 386–412 (1993).

(List continued on next page.)

*Primary Examiner*—Gollamudi S. Kishore
(74) *Attorney, Agent, or Firm*—Paul B. Simboli; Judy M. Mohr; Perkins Coie LLP

(57) ABSTRACT

Reagents for use in preparing a therapeutic liposome composition sensitized to a target cell are described. The reagents include a liposomal composition composed of pre-formed liposomes having an entrapped therapeutic agent and a plurality of targeting conjugates composed of a lipid, a hydrophilic polymer and a targeting ligand. The therapeutic, target-cell sensitized liposome composition is formed by incubating the liposomal composition with a selected conjugate.

25 Claims, 5 Drawing Sheets

OTHER PUBLICATIONS

Kirpotin, D., et al., "Liposomes with Detachable Polymer Coating: Destabilization and Fusion of Dioleoylphosphatidylethanolamine Vesicles Triggered by Cleavage of Surface-Grafted poly(ethylene glycol)" *FEBS Letters.* 388: 115–118 (1996).

Lear and Rafalski, "Peptide–Bilayer Interactions: Physical Measurements Related to Peptide Structure" *Viral Fusion Mechanisms*, J. Bentz (ed), CRC Press: Boca Raton, pp. 56–66 (1993).

Naka, K. et al., "Molecular Harpoons: Membrane–Disrupting Surfactants that Recognize Osmotic Stress," *J. Am. Chem. Soc.* 114: 4011–4013 (1992).

Sowers, A.E. (ed), *Cell Fusion*, Plenum Press: New York, p. 14 (1987).

Topchieva, I.N. and Efremova, N.V., "Conjugates of Proteins with Block Co–polymers of Ethylene and Propylene Oxides," *Biotechnology and Genetic Engineering Reviews.* 12: 357–382 (1994).

Kirpotin, D.B. et al., "Targeting of Liposomes to Solid Tumors: The Case of Sterically Stabilized Anti–HER2 Immunoliposomes," *Journal of Liposome Research.* 07(04): 391–417 (1997).

Park, J.W. et al., "Development of anti–p185$^{HER2}$ Immunoliposomes for Cancer Therapy," *Proc. Natl. Acad. Sci. USA.* 92: 1327–1331.

Uster, P.S. et al., "Insertion of Poly(Ethylene Glycol) Derivatized Phospholipid into Pre–formed Liposomes Results in Prolonged in vivo Circulation Time," *FEBS Letters.* 386: 243–246 (1996).

Zalipsky, S. et al., "Poly(Ethlyene Glycol)–Grafted Liposomes with Oligopeptide or Oligosaccharide Ligands Appended to the Termini of the Polymer Chains," *Bioconjugate Chem.* 08:111–118 (1997).

0 hour incubation 3 hour incubation 1 hour incubation 5 hour incubation

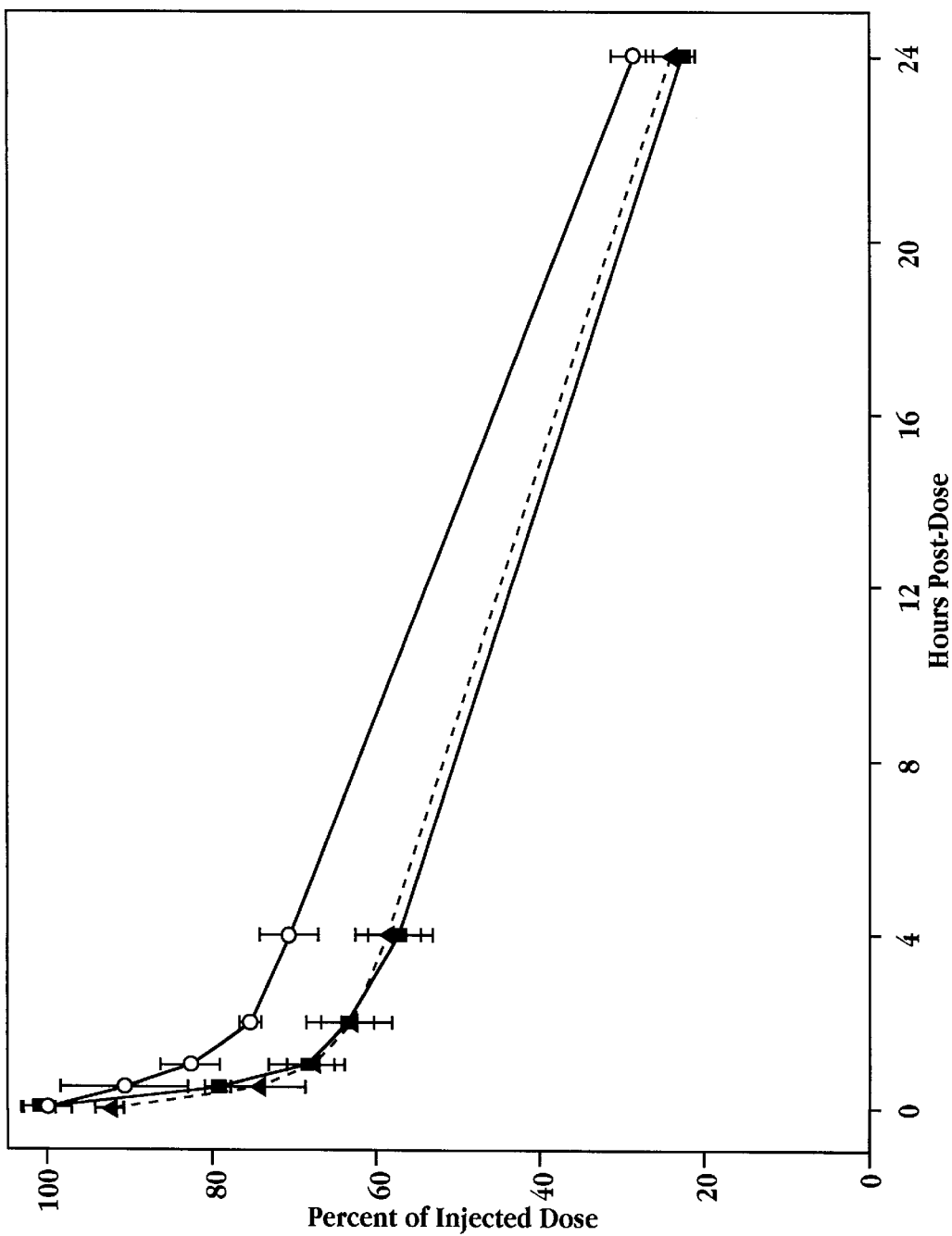

THERAPEUTIC LIPOSOME COMPOSITION AND METHOD OF PREPARATION

This application is a division of U.S. application Ser. No. 09/138,480 filed Aug. 21, 1998, now U.S. Pat. No. 6,056,973; which is a continuation-in-part of U.S. application Ser. No. 08/949,046, filed Oct. 10, 1997, now U.S. Pat. No. 5,891,468; which claims the priority of U.S. Provisional Application No. 60/028,269, filed Oct. 11, 1996, now abandoned, which are all incorporated herein by reference.

FIELD OF THE INVENTION

The present invention relates to a target-cell sensitized therapeutic liposome composition and to a method of preparing the composition. A library for preparation of the composition is also described.

BACKGROUND OF THE INVENTION

Liposomes, spherical, self-enclosed vesicles composed of amphipathic lipids, have been widely studied and are employed as vehicles for in vivo administration of therapeutic agents. In particular, the so-called long circulating liposomes formulations which avoid uptake by the organs of the mononuclear phagocyte system, primarily the liver and spleen, have found commercial applicability. Such long-circulating liposomes include a surface coat of flexible water soluble polymer chains, which act to prevent interaction between the liposome and the plasma components which play a role in liposome uptake.

More recently, efforts have focused on ways to achieve site specific delivery of long-circulating liposomes. In one approach, targeting ligands, such as an antibody, are attached to the liposomes' surfaces. This approach, where the targeting ligand is bound to the polar head group residues of liposomal lipid components, results in interference by the surface-grafted polymer chains, inhibiting the interaction between the bound ligand and its intended target (Klibanov, A. L., et al., *Biochim. Biophys. Acta.*, 1062:142–148 (1991); Hansen, C. B., et al., *Biochim. Biophys. Acta*, 1239:133–144 (1995)).

In another approach, the targeting ligand is attached to the free ends of the polymer chains forming the surface coat on the liposomes (Allen. T. M., et al., *Biochim. Biophys. Acta*, 1237:99–108 (1995); Blume, G., et al., *Biochim. Biophys. Acta*, 1149:180–184 (1993)). Two approaches have been described for preparing a liposome having a targeting ligand attached to the distal end of the surface polymer chains. One approach involves preparation of lipid vesicles which include an end-functionalized lipid-polymer derivative; that is, a lipid-polymer conjugate where the free polymer end is reactive or "activated". Such an activated conjugate is included in the liposome composition and the activated polymer ends are reacted with a targeting ligand after liposome formation. The disadvantage to this approach is the difficulty in reacting all of the activated ends with a ligand. The approach also requires a subsequent step for separation of the unreacted ligand from the liposome composition.

In another approach, the lipid-polymer-ligand conjugate is included in the lipid composition at the time of liposome formation. This approach has the disadvantage that some of the valuable ligand faces the inner aqueous compartment of the liposome and is unavailable for interaction with the intended target.

Both approaches suffer from a lack of flexibility in designing a therapeutic composition that is specific for a target cell for a specific patient. There is then a need for a liposome composition which provides flexibility in choice of the entrapped agent and the targeting ligand.

SUMMARY OF THE INVENTION

Accordingly, it is an object of the invention to provide a therapeutic liposome composition that is readily tailored and designed for a particular patient.

It is another object of the invention to provide a kit for formation of a therapeutic, target-cell sensitive liposome composition.

In one aspect, the invention includes a therapeutic liposome composition sensitized to a target cell, comprising
(i) a liposomal composition composed of pre-formed liposomes having an entrapped therapeutic agent; and
(ii) a plurality of conjugates, each conjugate composed of (a) a lipid having a polar head group and a hydrophobic tail, (b) a hydrophilic polymer having a proximal end and a distal end, where the polymer is attached at its proximal end to the head group of the lipid, and (c) a targeting ligand attached to the distal end of the polymer. The therapeutic, target-cell sensitized liposome composition is formed by combining the liposomal composition with a conjugate selected from the plurality of conjugates.

In one embodiment, the targeting ligand is an antibody or an antibody fragment. In one embodiment, the antibody or antibody fragment is of mouse origin and is humanized to remove murine epitopes.

In another embodiment, the targeting ligand specifically binds to an extracellular domain of a growth factor receptor. Such receptors are selected from c-erbB-2 protein product of the HER2/neu oncogene, epidermal growth factor receptor, basic fibroblast growth factor receptor, and vascular endothelial growth factor receptor.

In another embodiment, the targeting ligand binds a receptor selected from E-selectin receptor, L-selectin receptor, P-selectin receptor, folate receptor, CD4 receptor, CD19 receptor, $\alpha\beta$ integrin receptors and chemokine receptors.

The targeting ligand can also be folic acid, pyridoxal phosphate, vitamin B12, sialyl Lewis$^x$, transferrin, epidermal growth factor, basic fibroblast growth factor, vascular endothelial growth factor, VCAM-1, ICAM-1, PECAM-1, an RGD peptide or an NGR peptide.

The hydrophilic polymer surrounding the preformed liposomes is selected from the group consisting of polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, polyaspartamide and hydrophilic peptide sequences.

In one embodiment, the hydrophilic polymer is polyethylene glycol of molecular weight between 500–5,000 daltons.

The entrapped therapeutic agent is, in one embodiment, a cytotoxic drug. The drug can be an anthracycline antibiotic selected from doxorubicin, daunorubicin, epirubicin and idarubicin and analogs thereof.

The cytotoxic agent can also be a platinum compound selected from cisplatin, carboplatin, ormaplatin, oxaliplatin, zeniplatin, enloplatin, lobaplatin, spiroplatin, ((−)-(R)-2-aminomethylpyrrolidine (1,1-cyclobutane dicarboxylato) platinum), (SP-4-3(R)-1,1-cyclobutane-dicarboxylato(2-)-(2-methyl-1,4-butanediamine-N,N')platinum), nedaplatin and (bis-acetato-ammine-dichloro-cyclohexylamine-platinum(IV)).

In another embodiment, the cytotoxic agent is a topoisomerase 1 inhibitor selected from the group consisting of topotecan, irinotecan, (7-(4-methylpiperazino-methylene)-10,11-ethylenedioxy-20(S)-camptothecin), 7-(2-(N-isopropylamino)ethyl)-(20S)-camptothecin, 9-aminocamptothecin and 9-nitrocamptothecin.

In another embodiment, the cytotoxic agent is a vinca alkaloid selected from the group consisting of vincristine, vinblastine, vinleurosine, vinrodisine, vinorelbine and vindesine.

In another embodiment, the entrapped agent is a nucleic acid. The nucleic acid can be an antisense oligonucleotide or ribozyme or a plasmid containing a therapeutic gene which when internalized by the target cells achieves expression of the therapeutic gene to produce a therapeutic gene product.

In another aspect, the invention includes a plurality of targeting conjugates for use in preparing a targeted, therapeutic liposome composition. Each conjugate is composed of a (i) a lipid having a polar head group and a hydrophobic tail, (ii) a hydrophilic polymer having a proximal end and a distal end, the polymer attached at its proximal end to the head group of the lipid, and (iii) a targeting ligand attached to the distal end of the polymer.

The lipid in the conjugates is, in one embodiment, distearoyl phosphatidylethanolamine, distearoyl-phosphatidylcholine, monogalactosyl diacylglycerols or digalactosyl diacylglycerols.

The hydrophilic polymer in the conjugates is selected from the group consisting of polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, polyaspartamide and hydrophilic peptide sequences.

The targeting ligand of the conjugates can be any of those recited above.

In another aspect, the invention includes a method of formulating a therapeutic liposome composition having sensitivity to a target cell. The method includes the steps of (i) selecting a liposome formulation composed of pre-formed liposomes having an entrapped therapeutic agent; (ii) selecting from a plurality of targeting conjugates a targeting conjugate composed of (a) a lipid having a polar head group and a hydrophobic tail, (b) a hydrophilic polymer having a proximal end and a distal end, where the polymer is attached at its proximal end to the head group of the lipid, and (c) a targeting ligand attached to the distal end of the polymer; and (iii) combining the liposome formulation and the selected targeting conjugate to form said therapeutic, target-cell sensitive liposome composition.

In one embodiment, combining includes incubating under conditions effective to achieve insertion of the selected targeting conjugate into the liposomes of the selected liposome formulation.

In another embodiment, selecting a liposome formulation includes determining the sensitivity of the target cell to the therapeutic activity of the entrapped therapeutic agent.

In another embodiment, selecting a targeting conjugate includes determining the ability of the targeting ligand to bind cell surface receptors expressed on the target cell.

In another embodiment, selecting a targeting conjugate is based on (i) the ability of a targeting ligand to bind to cell surface receptors expressed on the target cell and (ii) the ability of the target cell to internalize liposomes bound to the target cell by binding between the target cell and the targeting ligand.

These and other objects and features of the invention will be more fully appreciated when the following detailed description of the invention is read in conjunction with the accompanying drawings.

BRIEF DESCRIPTION OF THE DRAWINGS

FIG. 4 is a plot showing the blood circulation lifetime of target-cell sensitized liposome prepared in accordance with the invention, where the percent of injected dose in vivo for liposomes having E-selectin Fab fragments targeting ligands (30 ligands per liposome represented by solid triangles, 70 ligands per liposome represented by solid squares) and for liposomes having a surface coating of polyethyleneglycol chains (open circles) as a function of time after dosing; FIG. 5A is the control of the untreated blood vessels under transmitted light, and FIG. 5B is a fluorescence micrograph showing binding of fluorsecin-labeled liposomes bearing an E-selectin Fab fragments to endothelial cells in the blood vessels.

DETAILED DESCRIPTION OF THE INVENTION

I. Definitions

Unless otherwise indicated, the terms below have the following meaning:

"Incubating" or "incubating under conditions effective to achieve insertion" refer to conditions of time, temperature and liposome lipid composition which allow for penetration and entry of a selected component, such as a lipid or lipid conjugate, into the lipid bilayer of a liposome.

"Pre-formed liposomes" refers to intact, previously formed unilamellar or multilamellar lipid vesicles.

"Sensitized to a target cell" or "target-cell sensitized" refers to a liposome which includes a ligand or moiety covalently bound to the liposome and having binding affinity for a receptor expressed on a particular cell.

"Therapeutic liposome composition" refers to liposomes which include a therapeutic agent entrapped in the aqueous spaces of the liposomes or in the lipid bilayers of the liposomes.

"Vesicle-forming lipid" refers to any lipid capable of forming part of a stable micelle or liposome composition and typically including one or two hydrophobic acyl hydrocarbon chains or a steroid group and may contain a chemically reactive group, such as an amine, acid, ester, aldehyde or alcohol, at its polar head group.

I. Liposome and Conjugate Library

Figure 1:
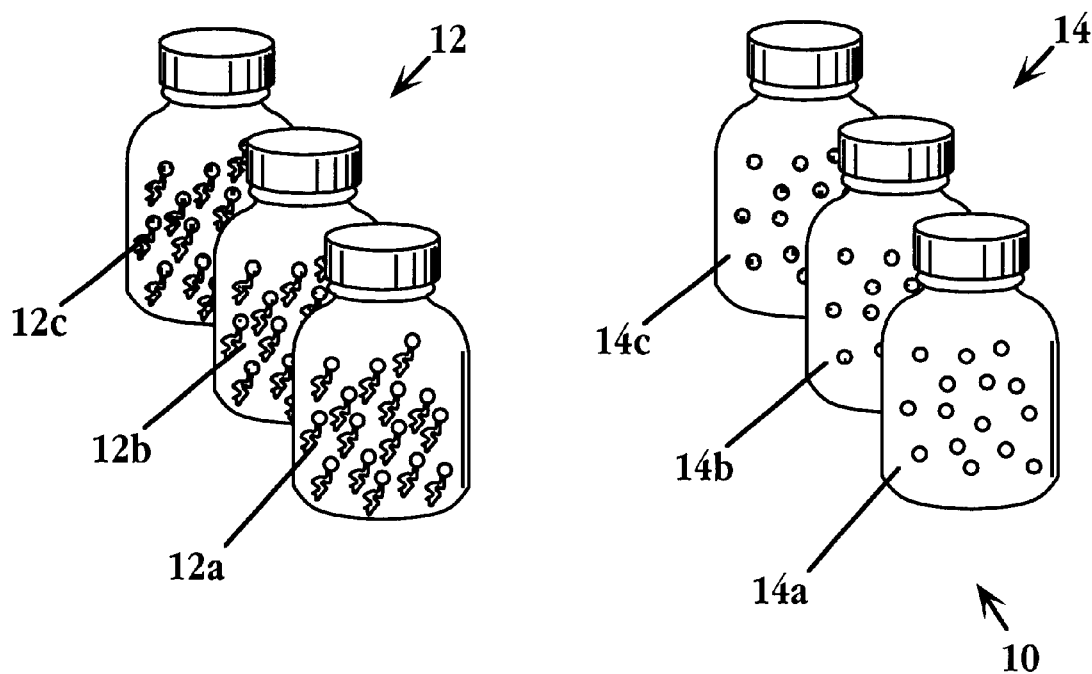
FIG. 1 illustrates a library composed of a plurality of therapeutic pre-formed liposomes and a plurality of targeting conjugates.

In one aspect, the invention includes a kit or "library" for preparation of a therapeutic, target-cell sensitized liposome composition. FIG. 1 shows such a library 10, where a plurality 12 of targeting conjugates 12(*a*), 12(*b*), 12(*c*), etc. and a plurality 14 of pre-formed therapeutic liposome compositions, such compositions 14(*a*), 14(*b*), 14(*c*) are shown. The targeting conjugates and pre-formed liposome pluralities are shown in suspension form in vials ready for use, however it will be appreciated that other storage forms are contemplated, such as lyophilized or freeze-dried.

The targeting conjugates in the library are lipid-polymer-ligand conjugates and will be described in more detail below. The conjugates in the library differ in the targeting ligand attached to the lipid-polymer, as well as in the lipid and polymer components. Exemplary ligands and lipid and polymer components will be set forth below.

The pre-formed liposomes in the library are either conventional liposomes containing an entrapped therapeutic agent or are liposomes having a surface coating of hydrophilic polymer chains, as will be described below. The pre-formed liposomes in the library differ from one another generally in the entrapped therapeutic agent and exemplary agents will be set forth below. The pre-formed liposomes can also differ from one another in the liposome lipid components.

A therapeutic, target-cell sensitized liposome composition is prepared from the library as follows. A composition specific for a subject suffering from a particular condition, for example a solid tumor of the lung, a bacterial infection or a viral infection, is prepared by selecting a targeting conjugate from the library. The targeting conjugate is selected either according to knowledge of those of skill in the art of ligand-receptor binding pairs or by obtaining a suitable patient sample, e.g., a fluid sample, a biopsy or the like. The sample is tested by means known to those in the art for expression of a variety of receptors to determine the appropriate targeting ligand.

A pre-formed therapeutic liposome composition is selected based on knowledge of those of skill in the art of the therapeutic agents appropriate for treatment of the particular condition. Alternatively, the therapeutic liposome composition is selected after performing chemosensitivity tests to determine the effect of the entrapped agent on cells of concern obtained from the patient biopsy or fluid sample.

Following selection of the targeting conjugate and of the pre-formed liposome composition, the target-cell sensitized, therapeutic liposome composition for the subject is prepared by combining the two components. As will be described, the components are combined under conditions effective to achieve insertion of the targeting conjugate into the liposome bilayer to create the target-cell sensitized liposomes. After insertion is complete, the composition is administered to patient.

The therapeutic pre-formed liposomes and the targeting conjugate will now be described in more detail.

A. Therapeutic Pre-formed Liposome Component

As discussed above, one component of the kit or library for preparing the composition of the invention is a plurality of pre-formed liposomes having an entrapped therapeutic or diagnostic agent. In this section, the liposome lipid components, exemplary agents and methods of preparing the liposomes are described.

1. Liposome Components

Liposomes suitable for use in the composition of the present invention include those composed primarily of vesicle-forming lipids. Such a vesicle-forming lipid is one which (a) can form spontaneously into bilayer vesicles in water, as exemplified by the phospholipids, or (b) is stably incorporated into lipid bilayers, with its hydrophobic moiety in contact with the interior, hydrophobic region of the bilayer membrane, and its head group moiety oriented toward the exterior, polar surface of the membrane.

The vesicle-forming lipids of this type are preferably ones having two hydrocarbon chains, typically acyl chains, and a head group, either polar or nonpolar. There are a variety of synthetic vesicle-forming lipids and naturally-occurring vesicle-forming lipids, including the phospholipids, such as phosphatidylcholine, phosphatidylethanolamine, phosphatidic acid, phosphatidylinositol, and sphingomyelin, where the two hydrocarbon chains are typically between about 14–22 carbon atoms in length, and have varying degrees of unsaturation. The above-described lipids and phospholipids whose acyl chains have varying degrees of saturation can be obtained commercially or prepared according to published methods. Other suitable lipids include glycolipids, cerebrosides and sterols, such as cholesterol.

Cationic lipids are also suitable for use in the liposomes of the invention, where the cationic lipid can be included as a minor component of the lipid composition or as a major or sole component. Such cationic lipids typically have a lipophilic moiety, such as a sterol, an acyl or diacyl chain, and where the lipid has an overall net positive charge. Preferably, the head group of the lipid carries the positive charge. Exemplary cationic lipids include 1,2-dioleyloxy-3-(trimethylamino) propane (DOTAP); N-[1-(2,3,-ditetradecyloxy)propyl]-N,N-dimethyl-N-hydroxyethylammonium bromide (DMRIE); N-[1-(2,3,-dioleyloxy)propyl]-N,N-dimethyl-N-hydroxyethylammonium bromide (DORIE); N-[1-(2,3-dioleyloxy)propyl]-N,N,N-trimethylammonium chloride (DOTMA); 3 [N-(N',N'-dimethylaminoethane)carbamoly]cholesterol (DC-Chol); and dimethyldioctadecylammonium (DDAB).

The cationic vesicle-forming lipid may also be a neutral lipid, such as dioleoylphosphatidyl ethanolamine (DOPE) or an amphipathic lipid, such as a phospholipid, derivatized with a cationic lipid, such as polylysine or other polyamine lipids. For example, the neutral lipid (DOPE) can be derivatized with polylysine to form a cationic lipid.

In another embodiment, the vesicle-forming lipid is selected to achieve a specified degree of fluidity or rigidity, to control the stability of the liposome in serum, to control the conditions effective for insertion of the targeting conjugate, as will be described, and to control the rate of release of the entrapped agent in the liposome.

Liposomes having a more rigid lipid bilayer, or a liquid crystalline bilayer, are achieved by incorporation of a relatively rigid lipid, e.g., a lipid having a relatively high phase transition temperature, e.g., up to 60° C. Rigid, i.e., saturated, lipids contribute to greater membrane rigidity in the lipid bilayer. Other lipid components, such as cholesterol, are also known to contribute to membrane rigidity in lipid bilayer structures.

On the other hand, lipid fluidity is achieved by incorporation of a relatively fluid lipid, typically one having a lipid phase with a relatively low liquid to liquid-crystalline phase transition temperature, e.g., at or below room temperature.

As will be described below, the targeted, therapeutic liposome composition of the invention is prepared using pre-formed liposomes and a targeting conjugate, which are incubated together under conditions effective to achieve insertion of the conjugate into the liposome bilayer. More specifically, the two components are incubated together under conditions which achieve insertion of the conjugate in such a way that the targeting ligand is oriented outwardly from the liposome surface, and therefore available for interaction with its cognate receptor.

Vesicle-forming lipids having phase transition temperatures from approximately 2° C.–80° C. are suitable for use in the pre-formed liposome component of the present composition. By way of example, the lipid distearyl phosphatidylcholine (DSPC) has a phase transition temperature of 62° C. and the lipid hydrogenated soy phosphatidylcholine (HSPC) has a phase transition temperature of 58° C. Phase transition temperatures of many lipids are tabulated in a variety of sources, such as Avanti Polar Lipids catalogue and Lipid Thermotropic Phase Transition Database (LIPIDAT, NIST Standard Reference Database 34).

In one embodiment of the invention, a vesicle-forming lipid having a phase transition temperature between about 30–70° C. is employed. In another embodiment, the lipid used in forming the liposomes is one having a phase transition temperature within about 20° C., more preferably 10° C., most preferably 5° C., of the temperature to which the ligand in the targeting conjugate can be heated without affecting its binding activity.

It will be appreciated that the conditions effective to achieve insertion of the targeting conjugate into the liposome are determined based on several variables, including, the desired rate of insertion, where a higher incubation temperature may achieve a faster rate of insertion, the temperature to which the ligand can be safely heated without affecting its activity, and to a lesser degree the phase transition temperature of the lipids and the lipid composition. It will also be appreciated that insertion can be varied by the presence of solvents, such as amphipathic solvents including polyethyleneglycol and ethanol, or detergents.

In one embodiment of the invention, the pre-formed liposomes also include a vesicle-forming lipid derivatized with a hydrophilic polymer. As has been described, for example in U.S. Pat. No. 5,013,556, including such a derivatized lipid in the liposome composition forms a surface coating of hydrophilic polymer chains around the liposome. The surface coating of hydrophilic polymer chains is effective to increase the in vivo blood circulation lifetime of the liposomes when compared to liposomes lacking such a coating.

Vesicle-forming lipids suitable for derivatization with a hydrophilic polymer include any of those lipids listed above, and, in particular phospholipids, such as distearoyl phosphatidylethanolamine (DSPE).

Hydrophilic polymers suitable for derivatization with a vesicle-forming lipid include polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, polyaspartamide and hydrophilic peptide sequences. The polymers may be employed as homopolymers or as block or random copolymers.

A preferred hydrophilic polymer chain is polyethyleneglycol (PEG), preferably as a PEG chain having a molecular weight between 500–10,000 daltons, more preferably between 1,000–5,000 daltons. Methoxy or ethoxy-capped analogues of PEG are also preferred hydrophilic polymers, commercially available in a variety of polymer sizes, e.g., 120–20,000 daltons.

Preparation of vesicle-forming lipids derivatized with hydrophilic polymers has been described, for example in U.S. Pat. No. 5,395,619. Preparation of liposomes including such derivatized lipids has also been described, where typically, between 1–20 mole percent of such a derivatized lipid is included in the liposome formulation.

2. Therapeutic Agent

The pre-formed liposomes include an agent entrapped in the liposome. Entrapped is intended to include encapsulation of an agent in the aqueous core and aqueous spaces of liposomes as well as entrapment of an agent in the lipid bilayer(s) of the liposomes.

Agents contemplated for use in the composition of the invention are widely varied, and include both therapeutic applications and those for use in diagnostic applications.

Therapeutic agents include natural and synthetic compounds having the following therapeutic activities: anti-arthritic, anti-arrhythmic, anti-bacterial, anticholinergic, anticoagulant, antidiuretic, antidote, antiepileptic, antifungal, anti-inflammatory, antimetabolic, antimigraine, antineoplastic, antiparasitic, antipyretic, antiseizure, antisera, antispasmodic, analgesic, anesthetic, beta-blocking, biological response modifying, bone metabolism regulating, cardiovascular, diuretic, enzymatic, fertility enhancing, growth-promoting, hemostatic, hormonal, hormonal suppressing, hypercalcemic alleviating, hypocalcemic alleviating, hypoglycemic alleviating, hyperglycemic alleviating, immunosuppressive, immunoenhancing, muscle relaxing, neurotransmitting, parasympathomimetic, sympathominetric plasma extending, plasma expanding, psychotropic, thrombolytic and vasodilating.

In a preferred embodiment, the entrapped agent is a cytotoxic drug, that is, a drug having a deleterious or toxic effect on cells. Exemplary cytotoxic agents include the anthracycline antibiotics such as doxorubicin, daunorubicin, epirubicin and idarubicin, and analogs of these, such as epirubidin and mitoxantrone; platinum compounds, such as cisplatin, carboplatin, ormaplatin, oxaliplatin, zeniplatin, enloplatin, lobaplatin, spiroplatin, ((−)-(R)-2-aminomethylpyrrolidine (1,1-cyclobutane dicarboxylato) platinum)(DWA2114R), (SP-4-3(R)-1,1-cyclobutane-dicarboxylato(2-)-(2-methyl-1,4-butanediamine-N,N') platinum) (CI-973), nedaplatin (254-S) and (bis-acetato-ammine-dichlorocyclohexylamine-platinum(IV)) (JM-216) (Weiss, R. B., et al., *Drugs*, 46(3):360–377 (1993)); and vinca alkaloids, such as vincristine, vinblastine, vinleurosine, vinrodisine, vinorelbine (navelbine) and vindesine.

Another preferred group of cytotoxic agents is a topoisomerase I inhibitor, such as camptothecin and its analogues, including SN-38 ((+)-(4S)-4,11-diethyl-4,9-dihydroxy-1H-pyrano[3',4':6,7]-indolizino[1,2-b]quinoline-3,14(4H,12H)-dione); 9-aminocamptothecin; 9-nitrocamptothecin, topotecan (hycamtin; 9-dimethyl-aminomethyl-10-hydroxycamptothecin); irinotecan (CPT-11; 7-ethyl-10-[4-(1-piperidino)-1-piperidino]-carbonyloxycamptothecin), which is hydrolyzed in vivo to SN-38); 7-ethylcamptothecin and its derivatives (Sawada, S. et al., *Chem. Pharm. Bull.*, 41(2):310–313 (1993)); 7-chloromethyl-10,11-methylene-dioxy-camptothecin; and others (SN-22, Kunimoto, T. et al., *J. Pharmacobiodyn.*, 10(3):148–151: (1987); DX-8951f and GG-211 ((7-(4-methylpiperazino-methylene)-10,11-ethylenedioxy-20(S)-camptothecin)) (Rothenberg, M. L., *Ann. Oncol.*, 8(9):837–855 (1997)), and 7-(2-(N-isopropylamino)ethyl)-(20S)-camptothecin (Chong Kun Dang Corp., Seoul Dorea, CKD602).

In another embodiment, the entrapped therapeutic agent is an angiogenesis inhibitor, such as angiostatin, endostatin and TNFα.

In another embodiment, the entrapped therapeutic agent in a nucleic acid, selected from a variety of DNA and RNA based nucleic acids, including fragments and analogues of these. A variety of genes for treatment of various conditions have been described, and coding sequences for specific genes of interest can be retrieved from DNA sequence databanks, such as GenBank or EMBL. For example, polynucleotides for treatment of viral, malignant and inflammatory diseases and conditions, such as, cystic fibrosis, adenosine deaminase deficiency and AIDS, have been described. Treatment of cancers by administration of tumor suppressor genes, such as APC, DPC4, NF-1, NF-2, MTS1, RB, p53, WT1, BRCA1, BRCA2 and VHL, are contemplated.

Administration of the following nucleic acids for treatment of the indicated conditions are also contemplated: HLA-B7, tumors, colorectal carcinoma, melanoma; IL-2, cancers, especially breast cancer, lung cancer, and tumors; IL-4, cancer; TNF, cancer; IGF-1 antisense, brain tumors; IFN, neuroblastoma; GM-CSF, renal cell carcinoma; MDR-1, cancer, especially advanced cancer, breast and ovarian cancers; and HSV thymidine kinase, brain tumors, head and neck tumors, mesothelioma, ovarian cancer.

The polynucleotide can be an antisense DNA oligonucleotide composed of sequences complementary to its target, usually a messenger RNA (mRNA) or an mRNA precursor. The mRNA contains genetic information in the functional, or sense, orientation and binding of the antisense oligonucleotide inactivates the intended mRNA and prevents its translation into protein. Such antisense molecules are determined based on biochemical experiments showing that proteins are translated from specific RNAs and once the sequence of the RNA is known, an antisense molecule that will bind to it through complementary Watson-Crick base pairs can be designed. Such antisense molecules typically contain between 10–30 base pairs, more preferably between 10–25, and most preferably between 15–20.

The antisense oligonucleotide can be modified for improved resistance to nuclease hydrolysis, and such analogues include phosphorothioate, methylphosphonate, phosphodiester and p-ethoxy oligonucleotides (WO 97/07784).

The entrapped agent can also be a ribozyme or catalytic RNA.

3. Liposome Preparation

The liposomes may be prepared by a variety of techniques, such as those detailed in Szoka, F., Jr., et al., *Ann. Rev. Biophys. Bioeng.* 9:467 (1980), and specific examples of liposomes prepared in support of the present invention will be described below. Typically, the liposomes are multilamellar vesicles (MLVs), which can be formed by simple lipid-film hydration techniques. In this procedure, a mixture of liposome-forming lipids of the type detailed above dissolved in a suitable organic solvent is evaporated in a vessel to form a thin film, which is then covered by an aqueous medium. The lipid film hydrates to form MLVs, typically with sizes between about 0.1 to 10 microns.

As described above, in one embodiment, the pre-formed liposomes include a vesicle-forming lipid derivatized with a hydrophilic polymer to form a surface coating of hydrophilic polymer chains on the liposomes surface. Such a coating is preferably prepared by including between 1–20 mole percent of the derivatized lipid with the remaining liposome forming components, e.g., vesicle-forming lipids. Exemplary methods of preparing derivatized lipids and of forming polymer-coated liposomes have been described in co-owned U.S. Pat. Nos. 5,013,556, 5,631,018 and 5,395,619, which are incorporated herein by reference. It will be appreciated that the hydrophilic polymer may be stably coupled to the lipid, or coupled through an unstable linkage which allows the coated liposomes to shed the coating of polymer chains as they circulate in the bloodstream or in response to a stimulus.

The therapeutic or diagnostic agent of choice can be incorporated into liposomes by standard methods, including (i) passive entrapment of a water-soluble compound by hydrating a lipid film with an aqueous solution of the agent, (ii) passive entrapment of a lipophilic compound by hydrating a lipid film containing the agent, and (iii) loading an ionizable drug against an inside/outside liposome pH gradient. Other methods, such as reverse evaporation phase liposome preparation, are also suitable.

Polynucleotides, oligonucleotides, other nucleic acids, such as a DNA plasmid, can be entrapped in the liposome by condensing the nucleic acid in single-molecule form. The nucleic acid is suspended in an aqueous medium containing protamine sulfate, spermine, spermidine, histone, lysine, mixtures thereof, or other suitable polycationic condensing agent, under conditions effective to condense the nucleic acid into small particles. The solution of condensed nucleic acid molecules is used to rehydrate a dried lipid film to form liposomes with the condensed nucleic acid in entrapped form. A similar approach to condensing nucleic acids for entrapment in liposomes is described in co-pending U.S. patent application Ser. No. 09/103,341.

The pre-formed liposomes of the invention are preferably prepared to have substantially homogeneous sizes in a selected size range, typically between about 0.01 to 0.5 microns, more preferably between 0.03–0.40 microns. One effective sizing method for REVs and MLVs involves extruding an aqueous suspension of the liposomes through a series of polycarbonate membranes having a selected uniform pore size in the range of 0.03 to 0.2 micron, typically 0.05, 0.08, 0.1, or 0.2 microns. The pore size of the membrane corresponds roughly to the largest sizes of liposomes produced by extrusion through that membrane, particularly where the preparation is extruded two or more times through the same membrane. Homogenization methods are also useful for down-sizing liposomes to sizes of 100 nm or less (Martin, F. J., in *SPECIALIZED DRUG DELIVERY SYSTEMS-MANUFACTURING AND PRODUCTION TECHNOLOGY*, (P. Tyle, Ed.) Marcel Dekker, New York, pp. 267–316 (1990)).

B. Targeting Conjugates

The kit or library of the invention also includes a targeting conjugate, now to be described. The targeting conjugate is composed of (i) a lipid having a polar head group and a hydrophobic tail, e.g., a vesicle-forming lipid and any of those described above are suitable; (ii) a hydrophilic polymer attached to the head group of the vesicle-forming lipid, and any of the polymers recited above are suitable; and (iii) a targeting ligand attached to the polymer.

The targeting ligand for use in the conjugate can be selected from a wide variety of moieties capable of targeting the pre-formed liposomes to a selected cell or tissue. Examples of suitable ligands suitable are listed in Table 1.

TABLE 1

| LIGAND-RECEPTOR PAIRS AND ASSOCIATED TARGET CELL | | |
|---|---|---|
| LIGAND | RECEPTOR | CELL TYPE |
| Folate | folate receptor | epithelial carcinomas, bone marrow stem cells |
| water soluble vitamins | vitamin receptor | various cells |
| Pyridoxyl phosphate | CD4 | CD4+ lymphocytes |
| Apolipoproteins | LDL | liver hepatocytes, vascular endothelial cells |

TABLE 1-continued

LIGAND-RECEPTOR PAIRS AND ASSOCIATED TARGET CELL

| LIGAND | RECEPTOR | CELL TYPE |
|---|---|---|
| Insulin | insulin receptor | pancreatic islet cells |
| Transferrin | Transferrin receptor | endothelial cells (brain) |
| Galactose | Asialyglycoprotein receptor | liver hepatocytes |
| Sialyl-Lewis$^x$ | E, P selectin | activated endothelial cells |
| Mac-1 | L selectin | neutrophils, leukocytes |
| VEGF | Flk-1,2 | tumor epithelial cells |
| basic FGF | FGF receptor | tumor epithelial cells |
| EGF | EGF receptor | epithelial cells |
| VCAM-1 | $\alpha_4\beta_1$ integrin | vascular endothelial cells |
| ICAM-1 | $\alpha_L\beta_2$ integrin | vascular endothelial cells |
| PECAM-1/CD31 | $\alpha_v\beta_3$ integrin | vascular endothelial cells |
| Fibronectin | $\alpha_v\beta_3$ integrin | activated platelets |
| Osteopontin | $\alpha_v 1$ and $\alpha_v\beta_5$ integrins | endothelial cells and smooth muscle cells in atherosclerotic plaques |
| RGD peptides and peptide mimetics (i.e. amino acid sequences of matrix proteins) | $\alpha_v\beta_3$ integrin | tumor endothelial cells, vascular smooth muscle cells |
| HIV GP 120/41 or GP120 C4 domain peptomers | CD4 | CD4 + lymphocytes |
| HIV GP120/41 (Macrophage tropic isolates) | Chemokine receptor CC-CRK-5 | macrophages, dendritic cells |
| Anti-cell surface receptor antibodies (or fragments thereof), such as anit-HER2/neu, anti-selectin, anti- | Cell surface receptors | erythrocytes, platelets endothelial cells, lymphocytes, tumors |
| Anti-cell surface receptor antibodies (or fragments thereof) | Cell surface receptors such as CD34, CD19, CD4 CD7, CDB, CD20, CD22 | bone marrow stem cells, malignant B and T cells |

One preferred ligand is an antibody or an antibody fragment. It will be appreciated that the antibody or antibody fragment can be of mouse origin and humanized to remove murine surface recognition features.

In another preferred embodiment, the targeting ligand binds to an extracellular domain of a growth factor receptor. Exemplary receptors include the c-erbB-2 protein product of the HER2/neu oncogene, epidermal growth factor (EGF) receptor, basic fibroblast growth receptor (basic FGF) receptor and vascular endothelial growth factor receptor, E-, L- and P-selectin receptors, folate receptor, CD4 receptor, CD19 receptor, $\alpha\beta$ integrin receptors and chemokine receptors.

1. Preparation of Targeting Conjugates

As described above, the targeting ligand is covalently attached to the free distal end of the hydrophilic polymer chain, which is attached at its proximal end to a vesicle-forming lipid. There are a wide variety of techniques for attaching a selected hydrophilic polymer to a selected lipid and activating the free, unattached end of the polymer for reaction with a selected ligand, and in particular, the hydrophilic polymer polyethyleneglycol (PEG) has been widely studied (Allen, T. M., et al., *Biochemicia et Biophysica Acta* 1237:99–108 (1995); Zalipsky, S., *Bioconjugate Chem.*, 4(4):296–299 (1993); Zalipsky, S., et al., *FEBS Lett.* 353:71–74 (1994); Zalipsky, S., et al., *Bioconjugate Chemistry*, 705–708 (1995); Zalipsky, S., in *STEALTH LIPOSOMES* (D. Lasic and F. Martin, Eds.) Chapter 9, CRC Press, Boca Raton, Fla. (1995)).

Generally, the PEG chains are functionalized to contain reactive groups suitable for coupling with, for example, sulfhydryls, amino groups, and aldehydes or ketones (typically derived from mild oxidation of carbohydrate portions of an antibody) present in a wide variety of ligands (see Table 1). Examples of such PEG-terminal reactive groups include maleimide (for reaction with sulfhydryl groups), N-hydroxysuccinimide (NHS) or NHS-carbonate ester (for reaction with primary amines), hydrazide or hydrazine (for reaction with aldehydes or ketones), iodoacetyl (preferentially reactive with sulfhydryl groups) and dithiopyridine (thiol-reactive). Synthetic reaction schemes for activating PEG with such groups are set forth in U.S. Pat. Nos. 5,631,018, 5,527,528, 5,395,619, and the relevant sections describing synthetic reaction procedures are expressly incorporated herein by reference.

It will be appreciated that any of the hydrophilic polymers recited above in combination with any of the vesicle-forming lipids recited above can be employed for the targeting conjugate and suitable reaction sequences can be determined by those of skill in the art.

II. Preparation of the Liposome Composition

The section above described preparation of the components in the library of the invention, namely the pre-formed liposomes and the targeting conjugates. This section describes preparation of the target-cell sensitized, therapeutic liposome composition using these two components.

As discussed briefly above, a pre-formed therapeutic liposome composition and a targeting conjugate are selected from the library. The two components are combined under conditions effective to achieve insertion of the targeting conjugate into the liposome lipid bilayer to form the target-cell sensitized composition.

In studies performed in support of the invention, a targeting conjugate of the ligand sialyl-Lewis$^x$ was attached to PEG-DSPE according to known methods (DeFrees, S. A., et al., *J. Am. Chem. Soc.*, 118:6101–6104 (1996)). Sialyl-Lewis$^x$ can be used to target liposomes to cells expressing endothelial leukocyte adhesion molecule-1 (ELAM-1 or E-selectin) for delivery of a therapeutic agent to a site of inflammation. ELAM-1 is expressed on the surface of endothelial cells of blood vessels adjacent to sites of inflammation. ELAM-1 recognizes and binds the polysaccharide moiety sialyl-Lewis$^x$ which is present on surfaces of neutrophils, and recruits neutrophils to sites of inflammation.

Pre-formed liposomes were prepared as described in Example 1 and were composed of partially hydrogenated soy-bean phosphatidylcholine (PHPC), cholesterol and mPEG-DSPE in a molar ratio of 55:40:3. The liposomes were sized to a diameter of about 100 nm. The liposomes were incubated at 37° C. with 1.2 mole percent sialyl-Lewis$^x$-PEG-DSPE targeting conjugate to achieve insertion of the conjugate into the pre-formed liposomes.

Insertion of the conjugate into the liposomes was monitored by sampling the mixture and tracking the relative amounts of micellular conjugate and liposomes by size exclusion chromatography, and the results are shown in FIGS. 2A–2D.

Figure 2A:
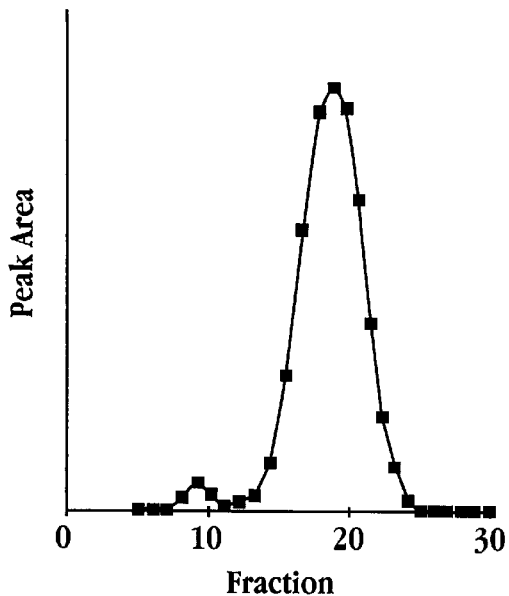
FIGS. 2A–2D are plots showing the fraction of liposomes (peak centered at fraction 10) and the fraction of micellular targeting conjugates (peak centered at fraction 20) by size exclusion chromatography from samples taken during incubation of a targeting conjugate sialyl-Lewis$^x$-PEG-DSPE with pre-formed liposomes at times of 0 hours (FIG. 2A), 1 hour (FIG. 2B), 3 hours (FIG. 2C) and 5 hours (FIG. 2D)
Figure 2C:
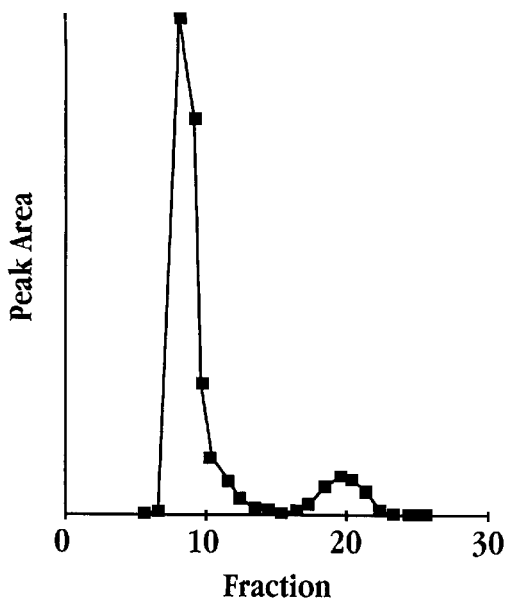
Figure 2B:
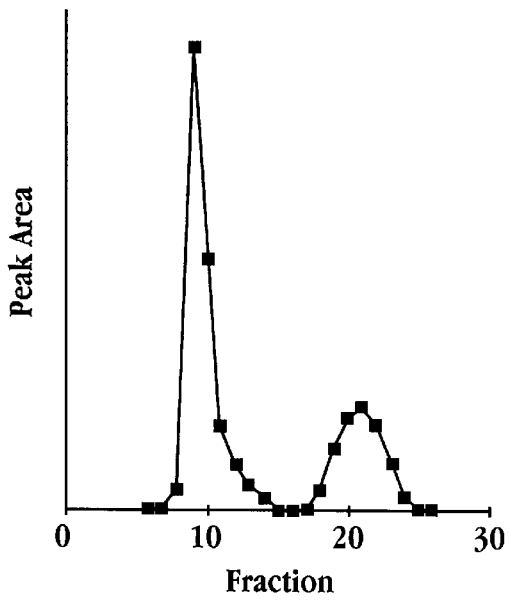
Figure 2D:
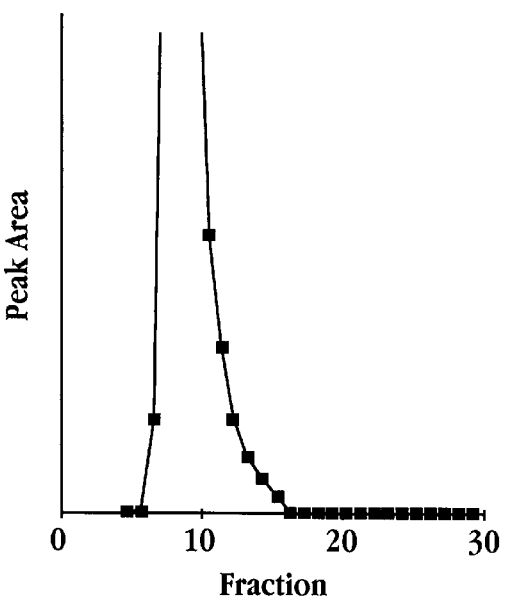

In FIGS. 2A–2D, the liposome fraction of the incubation mixture is represented by the peak centered around fraction 10 and the micellular targeting conjugate is represented by the peak centered around fraction 20. FIG. 2A shows the initial composition mixture, at time zero and FIGS. 2B–2D show the composition after 1, 3 and 5 hours incubation, respectively. Disappearance as a function of incubation time of the conjugate micelles (peak at fraction 20) is apparent, indicating insertion of the targeting conjugate into the pre-formed liposomes.

Figure 3:
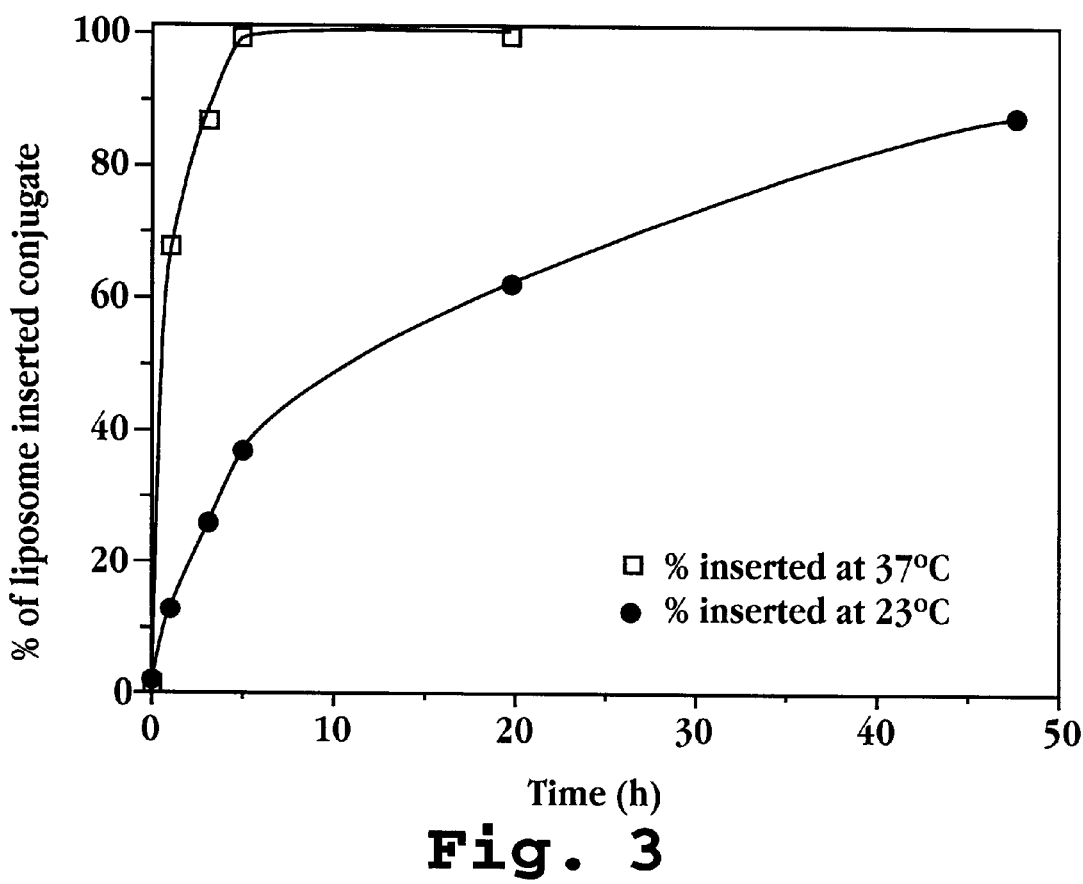
FIG. 3 is a plot showing the time course for insertion of the targeting conjugate sialyl-Lewis$^x$-PEG-DSPE into pre-formed liposomes when incubated at 25° C. (closed circles) and 37° C. (open squares)

FIG. 3 shows the time-course of insertion of sialyl-Lewis$^x$-PEG-DSPE targeting conjugate into PHPC:Chol:mPEG-DSPE (55:40:3) pre-formed liposomes at 37° C. (open squares) and 25° C. (closed circles). Insertion of the conjugate into the pre-formed liposomes proceeded more rapidly at 37° C., however insertion at ambient temperature was also substantial.

Other experiments in support of the invention were performed using the targeting conjugate YIGSRG-PDG-DSPE, prepared as described in Zalipsky, S., et al., *Bioconjugate Chemistry*, 8(2):111–118 (1997). The pentapeptide YIGSRG (Tyr-Ile-Gly-Ser-Arg) is the shortest fragment of the basement membrane glycoprotein laminin which retains binding activity to laminin cell surface receptors. In these studies, essentially the same time course of insertion was observed (data not shown) upon incubation with pre-formed liposomes of PHPC:cholesterol:mPEG-DSPE.

Table 2 shows the average particle size determined by dynamic light scattering after a 5 hour incubation period at 37° C. of pre-formed liposomes and a targeting conjugate, either YIGSRG-PEG-DSPE or sialyl-Lewis$^x$-PEG-DSPE. The average particle size after incubation and insertion of the targeting conjugate increased only slightly.

TABLE 2

| Targeting Conjugate | Liposome Size | |
|---|---|---|
| | Before insertion | After insertion |
| YIGSRG-PEG-DSPE | 100 nm | 105 nm |
| Sialyl-Lewis$^x$-PEG-DSPE | 98 nm | 99 nm |

The studies above illustrate preparation of a target-cell sensitized liposome composition by incubating pre-formed liposomes with a ligand-polymer-lipid targeting conjugate. It will be appreciated that liposomes having any composition and any selected entrapped therapeutic agent can be used in conjunction with the desired targeting conjugate. The ligand-polymer-lipid conjugate readily inserts into pre-formed liposomes in a time and temperature dependent fashion, and, as will be appreciated, is variable according to the liposome and ligand compositions.

III. In vivo Administration of the Composition

Liposomes having an E-selectin Fab fragment targeting ligand were prepared in accordance with the invention for in vivo administration to rodents. As described in Example 2, an anti-E-selectin Fab fragment was conjugated to PEG-DSPE to form an E-selectin Fab-PEG-DSPE targeting conjugate. The targeting conjugate was incubated with pre-formed $^{111}$In-labelled-liposomes composed of partially hydrogenated soy phosphatidylcholine (PHPC), PEG-DSPE and cholesterol in a 55:40:3 molar ratio in an amount sufficient to obtain 12, 20, 33, 40 and 70 Fab residues per 100 nm liposome (Example 2B). The insertion procedure resulted in greater than 95% of the targeting conjugates being inserted into the pre-formed liposomes. In one embodiment of the invention, the insertion efficiency is greater than 90%, more preferably greater than 95%.

The liposomes containing 30 Fab residues per liposome and 70 Fab residues per liposome were administered to rats to determine the blood circulation lifetime of the liposomes. As a control, $^{111}$In-labelled-liposomes of PHPC, cholesterol and PEG-DSPE (molar ratio of 55:40:3) were administered. The results are shown in FIG. 4, where the liposomes having 70 Fab residues per liposome (solid squares) and 30 Fab residues per liposomes (solid triangles) have a pharmacokinetic profile similar to that of the control liposomes (open circles). As seen, 24 hours after administration, nearly 25% of the injected dose remains in circulation in the bloodstream.

Figure 5A:
FIGS. 5A–5B are scanned images of micrographs of blood vessels in a window chamber of a mouse dorsal fold, where
Figure 5B:
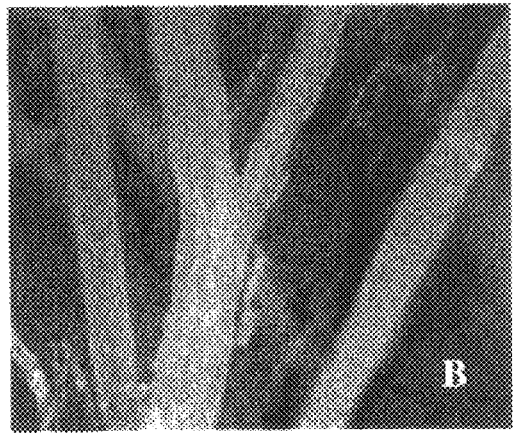

As described in Example 2C, pre-formed liposomes composed of hydrogenated soy phosphatidylcholine (HSPC), cholesterol, PEG-DSPE and fluorescein-labelled DHPE, in a molar ratio of 53.5/40/4/2.5, were incubated with the E-selectin-PEG-DSPE targeting conjugate at 37° C. for 1 hour. The fluorescein-labeled liposomes were administered to mice equipped with a dorsal skin fold window chamber. Endotoxin was applied topically in the window chamber 10 minutes after intravenous injection of the liposomes. FIGS. 5A–5B are scanned images of photomicrographs of the blood vessels under transmitted light prior to liposome administration (FIG. 5A) and 5 hours after administration of the target-cell sensitized, fluorescein-labeled liposomes (FIG. 5B).

As can be seen in FIG. 5B, the E-selectin Fab liposomes target the endothelial cells along the blood vessels. The appearance of E-selectin antigen peak was around 5 hours after endotoxin treatment, indicating that the binding activity of the E-selectin antibody was retained.

IV. Method of Using the Library

In accordance with the invention, a plurality of targeting conjugates and a plurality of liposome formulations with a variety of entrapped therapeutic agents are available for selection according to the indication to be treated. In this section, preparation and use of the library will be further demonstrated by describing suitable library components for treatment of an exemplary indication, breast cancer.

For treatment of human breast cancer, the library of the invention includes a plurality of targeting conjugates in the form of pre-filled vials containing the conjugate as a purified, sterile micellar suspension in an appropriate buffer. The plurality of targeting conjugates can include the following.

1. anti c-erbB-2-PEG-DSPE

The c-erbB-2 receptor of the HER2-neu oncogene is over-expressed in many human breast cancer cells. Humanized monoclonal antibodies have been developed which bind with high affinity to the c-erbB-2 receptor (Baselga J., et al., *J Clin Oncol.*, 14(3):737–44 (1996)). Single chain sFv fragments of the anti c-erbB-2 C6.5 antibody into which a terminal cysteine group is inserted are obtained as described by Schier et al. (*Immunotechnology*, 1(1):73–81 (1995)). The whole c-erbB-2 antibody is conjugated to PEG-DSPE having a reactive hydrazide moiety. The sFv fragment containing the terminal cysteine (and thus a free thiol group) is conjugated to PEG-DSPE-maleimide, under conditions like those described for the conjugation of the anti-E selected Fab' antibody fragment to the same compound in Example 2.

2. anti-EGFR-PEG-DSPE Targeting Conjugate

Epidermal Growth Factor Receptor (EGFR) and a deletion-mutant form of EGFR (EGFRvIII) are over-expressed in certain breast cancers, gliomas and lung tumors (Beckmann, M. W., *Geburtshilfe Frauenheilkd*, 55(5):258–65 (1995)). Whole mouse monoclonal antibodies which bind this receptor are obtained as described by Wikstrand et al (*Cancer Res.*, 55(14):3140–8 (1995)). These whole antibodies are conjugated to DSPE-PEG having an active hydrazide end as has been described in the art.

It will be appreciated that other antibody or antibody fragments which are known to bind receptors over-expressed in breast cancers cells including integrins such as $a_vB_5$ and interlukin-8 are available and can be linked to PEG-DSPE for preparation of targeting conjuates for use in the library.

3. PEG-DSPE Targeting Conjugates Including $a_v$ Integrin-binding RGD Peptides Proteins that contain the Arg-Gly-Asp (RGD) attachment site, together with the integrins that serve as receptors for them, constitute a major recognition system for cell adhesion. The RGD sequence is the cell attachment site for proliferating vascular endothelial cells which form the blood supply to tumors (during angiogenesis). Such attachments are mediated by $a_v$ integrins expressed by these endothelial cells. The integrin-binding activity of matrix adhesion proteins can be reproduced by short synthetic peptides containing the RGD sequence. Reagents that bind selectively to only one or a few of the RGD-directed integrins can be designed by cyclizing peptides with selected sequences around the RGD and by synthesizing RGD mimics. Such RGD peptides can be isolated by using phage display peptide libraries (Pasqualini, R., and Ruoslahti, E., *Nature*, 380(6572):364–6 (1996)). Two of these peptides—one containing an $a_v$ integrin-binding Arg-Gly-Asp motif and the other an Asn-Gly-Arg motif—have been identified that bind selectively to tumor vasculature. These can be linked to liposomes using the methods described herein.

As can be appreciated, a plurality of other PEG-DSPE conjugates of ligands, such as folate or transferin, which may bind to receptors on human breast cancer cells are prepared according to the examples set herein and by methods known in the art.

Continuing with the example of using the library for treatment of human breast cancer, the library further includes a therapeutic liposome composition or a plurality of liposome compositions containing encapsulated agents appropriate for treating human breast cancer cells in vivo. The pre-formed liposomes are in the form of pre-filled vials containing the liposomes as a sterile suspension in appropriate buffers is created. Liposome containing the following entrapped agents are exemplary for the human breast cancer example: doxorubicin, cisplatin, water-soluble camptothecin derivatives (e.g. topotecan) navelbine, vincristine, antisense oligonucleotides, p53 gene, HSVtk gene, a radiation sensitizer or an angiogenesis inhibitor.

To use the library, a targeting conjugate and a therapeutic liposome composition are selected. Selection of the targeting conjugate is based upon the expression of the conjugate's cognate receptor on individual patient's breast cancer cells. For example, it is common to test for the expression of a variety of receptors on cancer cells obtained from patients during biopsy. Clinical reference laboratories routinely screen biopsy specimens for estrogen receptor status and c-erbB-2 expression status is becoming routine with the clinical development of HERCEPTIN an anti-tumor therapeutic antibody product described by Baselga, et al, (*J. Clin Oncol.*, (3):737–44 (1996)). Exemplary methods for determining c-erbB-2 receptor status are given by Sjogren, et al. (*J Clin Oncol.*,16(2):462–9 (1998)). Patients whose tumors overexpress c-erbB-2 receptor are identified by this approach. EGFR receptor status is determined by similar methodology (Newby, J. C. et al., *Br J Cancer.*,71(6):1237–42 (1995)). Expression of other receptors is determined by similar methodology.

Next, a pre-formed therapeutic liposome composition is selected from the library. A variety of methods exist to screen for the sensitivity of breast cancer cells taken at biopsy to the cell killing effects of drugs in vitro and in vivo (chemosensitivity testing) and exemplary methods are described by Tomikawa, et al. (*Anticancer Res.*, 18(2A):1059–62 (1998)) and by Coley, et al. (*Anticancer Res.* 17(1A):231–6 (1997)) and by Andreotti, et al. (*Cancer Res.*, 55(22):5276–82 (1995)). In vitro cytotoxicity is often expressed as the concentration of a particular cancer drug needed to inhibit cancer cell proliferation by 50% in culture ($IC_{50}$). In a typical screening test, cells obtained from a patient's biopsy specimen are teased apart (mechanically and/or by enzyme treatment), suspended in a medium which supports their growth and placed in wells of a culture plate. Drugs at various dilutions are added and any growth inhibition of the cells caused by the drug is measured. $IC_{50}$ values are derived from these measurements. Drugs that kill the cells or inhibit growth at concentrations at or below $IC_{50}$ values that can be achieved in vivo are considered as candidates for therapeutic intervention.

In an alternative approach, a therapeutic agent can be selected on the basis of historical information and accepted clinical practice (see for example, Handbook of Cancer Chemotherapy, $3^{rd}$ edition, R. T. Skeell, editor, A, Little Brown, Boston, 1991, pp 77–138.). For example, doxorubicin is known to be one of the most active agents against human breast cancer. Therefore, in a plurality of liposome-encapsulated cancer drugs, doxorubicin would represent an obvious selection for the treatment of breast cancer based on accepted clinical practice.

After selection of the targeting conjugate and the therapeutic pre-formed liposome composition, the two reagents are combined to create target cell-sensitized therapeutic liposome composition tailored to an individual patient's cancer. The contents of the vial containing the conjugate and the vial containing the pre-formed therapeutic liposome composition, selected as described above and based upon the expression of the appropriate cell surface receptor and the sensitivity of the cell to growth inhibitory action of the encapsulated agent, are combined under the conditions described effective to achieve insertion of the conjugate into the liposome bilayer. Aseptic technique is used, preferably in a hospital pharmacy or other appropriate setting. Once the target-sensitized therapeutic liposome composition is formed, it is administered to the patient for which it was created. The liposomes are typically in suspension form and are administered parenterally, preferably intravenously. Other routes of administration are suitable, including subcutaneous, intramuscular, interlesional (to tumors), intertracheal by inhalation, topical, internasal, intraocular, via direct injection into organs and intravenous.

As can be appreciated, tailoring the formulation in this way to the individual patient maximizes the likelihood of therapeutic benefit provided by the targeting component and the encapsulated drug.

It will be appreciated that the dosage will depend on the liposome composition and the condition to be treated. Suitable dosages can be readily determined by those of skill in the art.

Use of the library will now be demonstrated for treatment of a patient suffering from a hematological disease, e.g. a B-cell or T-cell malignancy, such as B-cell leukemias/lymphomas, multiple myeloma, T-cell lymphoma and acute lymphocytic leukemia.

As described above, the library includes a plurality of targeting conjugates. Targeting conjugates suitable for selection include lipid-polymer-antibody conjugates, where the antibody is a monoclonal antibody or antibody fragment having a specific recognition to a B-cell or a T-cell epitope, as has been described in U.S. Pat. No. 5,620,689, which is incorporated herein by reference. For example, the antibody can be one that recognizes the B-cell epitopes CD19, CD20, CD22 or CD77. The antibody can be one that recognizes the T-cell epitopes CD4, CD7 or CD8.

The library further includes liposomes having entrapped agents. For treatment of hematological disorders, liposomes having the following entrapped agents are potential candidates for selection from the library: doxorubicin, vincristine, lomustine, interferon, melphalan, cyclophosphamide, prednisone, chlorambucil, carmustin and dexamethasone.

A blood or tissue sample is taken from the patient suffering from the hematological disorder for determination of the expression of various receptors, such as CD19, CD20, CD22, CD4, CD7, CD8. If the origin of the disorder is known to be either B-cell or T-cell, the receptor screening can of course be more selective, e.g., if the disorder is B-cell related, then the sample can be tested for expression of CD19, CD20 and CD22. Based on the results of the screening, a suitable targeting conjugate is chosen.

A therapeutic agent for treatment of the disorder is selected from the library using the procedures described in the breast cancer example above.

The selected conjugate and liposome composition are incubated together as described above to form the target-cell sensitized, therapeutic liposome composition specific for the patient. Suitable dosages for the composition can be initially based on the standard chemotherapeutic dose and adjusted accordingly over the course of treatment by monitoring the disease progression.

V. EXAMPLES

The following examples illustrate methods of preparing the composition of the present invention. The examples are in no way intended to limit the scope of the invention.

Example 1

Preparation of Pre-formed Liposomes and Insertion of Targeting Conjugate

Liposomes were prepared by mixing partially hydrogenated soy-bean phosphatiylcholine (PHPC, iodine value of 35, Lipoid (Ludwigshafen, Germany)), cholesterol (Croda (Fullerton, Calif.)) and mPEG-DSPE (prepared as described in Zalipsky, S., et al., *Bioconjugate Chemistry*, 4:296–299 (1993)) at a molar ratio of 55:40:3 in chloroform and/or methanol in a round bottom flask. The solvents were removed by rotary evaporation, and the dried lipid film produced was hydrated with either sodium phosphate buffer (10 mM, 140 mM NaCl, pH 7) or HEPES buffer (25 mM, 150 mM NaCl, pH 7) to produce large multilamellar vesicles. The resulting vesicles were passed repeatedly under pressure through 0.2, 0.1 and 0.05 m pore size polycarbonate membranes, until the average size distribution for the diameter (monitored by dynamic light scattering using a Coulter N4MD (Hialeah, Fla.)) was approximately 100 nm. The mean particle diameter measured from 12 different batches ranged form 92 to 111 nm with an average 98 nm.

Targeting conjugates of and YIGSRG-PEG-DSPE were prepared according to Zalipsky, S., et al., *Bioconjugate Chemistry*, 8(2):111–118 (1997).

The pre-formed liposomes were incubated at either 25° C. or 37° C. with 1.2 mole percent of one of the targeting conjugates. At various time points, targeting conjugates (micelles) were separated from inserted targeting conjugates (liposomes) by size exclusion chromatography. For the sialyl-Lewis$^x$-PEG-DSPE conjugate, a Biogel A50M column equilibrated with 10 mM sodium phosphate, 140 mM sodium chloride, and 0.02% NaN$_3$ at pH 6.5 was used. For YIGSRG-PEG-DSPE conjugate, a Sepharose 4B column was used with 10% sucrose and 10 mM HEPES at pH 7.0 as eluent. The results for the sialyl-Lewis$^x$-PEG-DSPE conjugate are shown in FIGS. 2A–2D for the 0, 1, 3 and 5 hour time points, where the peak centered around fraction 10 corresponds to the liposomes and the peak centered around fraction 20 corresponds to the micellular, targeting conjugate.

The collected fractions (1 mL) from the size exclusion chromatograph were diluted 1:10 in methanol, and analyzed for ligand content by HPLC (Shimadzu and Rainin systems), with the results shown in FIG. 3.

Example 2

Preparation of Anti-E-selectin Fab Conjugate and Insertion into Pre-formed Liposomes A. Preparation of the Targeting Conjugate An anti-E-selectin Fab fragment was conjugated to PEG-DSPE to form a targeting conjugate as follows. An aqueous solution of 750 mM 2-mercaptoethylamine as a reducing agent was prepared. 10 μl of the mercaptoethylamine was added to 1 ml of 5 mg/ml anti E-selectin Fab fragment in 50 mM sodium acetate and 125 mM NaCl, pH=5.0. The final concentration of reducing agent was 7.5 mM. The solution was incubated at 37° C. for 30 minutes. The excess reducing agent was removed on a 10DG-column (Bio-Rad) equilibrated with 25 mM HEPES/0.9% saline buffer. The collected fractions were analyzed spectrophotometrically to determine the fractions containing the Fab fragments. These fractions were pooled and diluted 1:50 in phosphate buffered saline to determine the protein concentration.

The Fab fragments (molecular weight of 3,000 Daltons) were mixed in a 1:1 molar ratio with PEG-DSPE (molecular weight 50,000 daltons) having an active maleimide end group (prepared as described in U.S. Pat. No. 5,527,528). The two components were incubated overnight at room temperature. The unreacted maleimide was quenched with 2 mM β-mercaptoethanol for 30 minutes at room temperature. The free Fab fragments and β-mercaptoethanol were separated from the Fab-PEG-DSPE conjugate on an S-200 column equilibrated in 25 mM HEPES/0.9% saline at pH 7.2. Fractions of 1 ml were collected and read on the spectrophotometer at 280 nm to determine the fractions containing the conjugate and the free Fab fragments. The fractions were pooled accordingly and the concentration of the Fab-PEG-DSPE micellular solution is determined spectrophotometrically (280 nm). The efficiency of conjugation of the Fab fragment to the maleimide-PEG-DSPE was approximately 40%.

B. Insertion of the Conjugate into Pre-formed Liposomes

Liposomes of partially hydrogenated soy phosphatidylcholine (PHPC), PEG-DSPE and cholesterol in a 55:40:3 molar ratio were prepared as described in Example 1. Depending on the desired number of targeting ligands per liposomes, an amount of the Fab-PEG-DSPE conjugate was added to a suspension of liposomes and incubated overnight at room temperature. A 100 μl aliquot of the insertion mixture was taken and placed on a SEPHAROSE 4B column (0.7×30 cm) to separate the free Fab conjugate from the liposomes. 1 ml fractions were collected and read on the spectrophotometer to determine the amount of conjugate inserted into the pre-formed liposomes. Greater than 95% of the conjugates were inserted into the pre-formed liposomes.

Following insertion of the targeting conjugate, an aliquot of the liposomes were analyzed by amino acid analysis to determine the protein concentration. Another aliquot was analyzed for phosphorus content. Based on these values, the amount of protein per liposome was determined.

Using this insertion procedure, liposomes containing 12, 20, 33, 40 and 70 Fab residues per 100 nm liposome, as determined by amino acid analysis, were prepared.

111In-labelled-liposomes containing 30 Fab residues per liposome and 70 Fab residues per liposome were administered to rats to determine the blood circulation lifetime of the liposomes. As a control, $^{111}$In-labelled-liposomes of PHPC, cholesterol and PEG-DSPE (molar ratio of 55:40:3) were administered. The results are shown in FIG. 4.

C. In vivo Targeting

E-selectin Fab-PEG-DSPE targeting conjugate was inserted into pre-formed liposomes as follows. The pre-formed liposomes were composed of hydrogenated soy phosphatidylcholine (HSPC), cholesterol and PEG-DSPE in a molar ratio of 53.5/40/4. The liposomes included 2.5 mole percent of the lipid marker of fluorescein-DHPE (Molecular Probes, Inc.). The pre-formed liposomes were incubated with the micellular solution of the targeting conjugate at 37° C. for 1 hour. The insertion mixture was placed on a Bio-Rad A 50 m column equilibrated with 25 mM HEPES/saline pH 7.2 and 0.5 ml fractions were collected. Spectrophotometric analysis of the fractions indicated that the insertion efficiency of the Fab targeting conjugate into the liposomes was approximately 100% after 2 hours at 37° C.

The fluorescein-labeled liposomes were administered to mice equipped with a window chamber in a dorsal skin fold. Endotoxin was applied topically in the window chamber 10 minutes after intravenous injection of the liposomes. FIGS. 5A–5B are photomicrographs (scanned images) of the blood vessels under transmitted light prior to liposome administration (FIG. 5A) and 5 hours after administration of the target-cell sensitized, fluorescein-labeled liposomes (FIG. 5B).

Although the invention has been described with respect to particular embodiments, it will be apparent to those skilled in the art that various changes and modifications can be made without departing from the invention.

What is claimed is:

1. A method of formulating a therapeutic liposome composition having sensitivity to a target cell, comprising selecting a liposome composition from a plurality of liposomal compositions comprised of pre-formed liposomes having an entrapped therapeutic agent;

selecting from a plurality of targeting conjugates a targeting conjugate comprised of (i) a lipid having a polar head group and a hydrophobic tail, (ii) a hydrophilic polymer having a proximal end and a distal end, said polymer attached at its proximal end to the head group of the lipid, and (iii) a targeting ligand attached to the distal end of the polymer; and combining the selected liposome composition and the selected targeting conjugate to form a therapeutic target-cell sensitive liposome composition.

2. The method of claim 1, wherein said combining includes incubating under conditions effective to achieve insertion of the selected targeting conjugate into the liposomes of the selected liposome composition.

3. The method of claim 1, wherein said selecting a liposome composition includes determining the sensitivity of the target cell to the therapeutic activity of the entrapped therapeutic agent.

4. The method of claim 1, wherein said selecting a targeting conjugate includes determining the ability of the targeting ligand to bind cell surface receptors expressed on the target cell.

5. The method of claim 4, wherein said selecting a targeting conjugate is based on (i) the ability of a targeting ligand to bind to cell surface receptors expressed on the target cell and (ii) the ability of the target cell to internalize liposomes bound to the target cell by binding between the target cell and the targeting ligand.

6. The method of claim 1, wherein the targeting ligand is an antibody or an antibody fragment.

7. The method of claim 6, wherein the antibody or antibody fragment is a humanized murine antibody.

8. The method of claim 6, wherein the targeting ligand specifically binds to an extracellular domain of a growth factor receptor.

9. The method of claim 8, wherein the receptors are selected from the group consisting of c-erbB-2 protein product of the HER2/neu oncogene, epidermal growth factor receptor, basic fibroblast growth factor receptor, and vascular endothelial growth factor receptor.

10. The method of claim 6, wherein the targeting ligand binds a receptor selected from the group consisting of E-selectin receptor, L-selectin receptor, P-selectin receptor, folate receptor, CD4 receptor, CD19 receptor, αβ integrin receptors and chemokine receptors.

11. The method of claim 1, wherein the targeting ligand binds a receptor on a malignant B-cell or T-cell, said receptor selected from the group consisting of CD19, CD20, CD22, CD4, CD7 and CD8.

12. The method of claim 1, wherein the targeting ligand is selected from the group consisting of folic acid, pyridoxal phosphate, vitamin B12, sialyl Lewis$^x$, transferrin, epidermal growth factor, basic fibroblast growth factor, vascular endothelial growth factor, VCAM-1, ICAM-1, PECAM-1, RGD peptides and NGR peptides.

13. The method of claim 1, wherein the hydrophilic polymer is selected from the group consisting of polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, polyaspartamide and hydrophilic peptide sequences.

14. The method of claim 1, wherein the hydrophilic polymer is polyethylene glycol.

15. The method of claim 14, wherein the polyethylene glycol has a molecular weight between 500–5,000 daltons.

16. The method of claim 1, wherein the liposomes further contain a cationic lipid.

17. The method of claim 1, wherein the entrapped therapeutic agent is a cytotoxic drug.

18. The method of claim 17 wherein the cytotoxic drug is an anthracycline antibiotic selected from the group consisting of doxorubicin, daunorubicin, epirubicin and idarubicin and analogs thereof.

19. The method of claim 17, wherein the cytotoxic agent is a platinum compound selected from cisplatin, carboplatin, ormaplatin, oxaliplatin, zeniplatin, enloplatin, lobaplatin, spiroplatin, ((−)-(R)-2-aminomethylpyrrolidine (1,1-cyclobutane dicarboxylato)platinum), (SP-4-3(R)-1,1-cyclobutanedicarboxylato(2-)-(2-methyl-1,4-butanediamine-N,N')platinum), nedaplatin and (bis-acetato-ammine-dichloro-cyclohexylamine-platinum(IV)).

20. The method of claim 17, wherein the cytotoxic agent is a topoisomerase 1 inhibitor selected from the group consisting of topotecan, irinotecan, (7-(4-methylpiperazino-methylene)-10,11-ethylenedioxy-20(S)-camptothecin), 7-(2-(N-isopropylamino)ethyl)-(20S)-camptothecin, 9-aminocamptothecin and 9-nitrocamptothecin.

21. The method of claim 17, wherein the cytotoxic agent is a vinca alkaloid selected from the group consisting of vincristine, vinblastine, vinleurosine, vinrodisine, vinorelbine and vindesine.

22. The method of claim 1, wherein the entrapped agent is a nucleic acid.

23. The method of claim 22, wherein the nucleic acid is an antisense oligonucleotide or ribozyme.

24. The method of claim 22, wherein the nucleic acid is a plasmid containing a therapeutic gene which when internalized by the target cells achieves expression of the therapeutic gene to produce a therapeutic gene product.

25. The method of claim 1, wherein said selecting a targeting conjugate includes selecting a micellar suspension of a targeting conjugate.

* * * * *